US012588914B2

(12) United States Patent
Cannon et al.

(10) Patent No.: US 12,588,914 B2
(45) Date of Patent: Mar. 31, 2026

(54) MENISCAL ALLOGRAFT TRANSPLANTATION SYSTEM AND METHODS FOR USE

(71) Applicant: Arthrex, Inc., Naples, FL (US)

(72) Inventors: Bryan Cannon, Miami, FL (US);
Robert Benedict, Naples, FL (US);
James Dunlop, Cape Coral, FL (US);
Marc Sedlaczek, Munich (DE);
Thomas R. Carter, Phoenix, AZ (US)

(73) Assignee: Arthrex, Inc., Naples, FL (US)

( * ) Notice: Subject to any disclaimer, the term of this patent is extended or adjusted under 35 U.S.C. 154(b) by 0 days.

(21) Appl. No.: 18/757,774

(22) Filed: Jun. 28, 2024

(65) Prior Publication Data

US 2025/0000523 A1      Jan. 2, 2025

Related U.S. Application Data

(60) Provisional application No. 63/511,254, filed on Jun. 30, 2023.

(51) Int. Cl.
| | |
|---|---|
| *A61B 17/16* | (2006.01) |
| *A61B 17/00* | (2006.01) |
| *A61B 17/15* | (2006.01) |
| *A61F 2/46* | (2006.01) |
| *A61L 27/36* | (2006.01) |
| *A61B 90/00* | (2016.01) |
| *A61M 25/09* | (2006.01) |

(52) U.S. Cl.
CPC .......... *A61B 17/1635* (2013.01); *A61B 17/15* (2013.01); *A61B 17/1604* (2013.01); *A61B 17/1622* (2013.01); *A61F 2/4644* (2013.01);
*A61L 27/3612* (2013.01); *A61B 2017/00969* (2013.01); *A61B 2090/034* (2016.02); *A61M 25/09041* (2013.01); *A61M 2025/09183* (2013.01)

(58) Field of Classification Search
CPC ............... A61B 17/1635; A61F 2/4644; A61F 2002/2839; A61F 2002/2835; A61F 2/3872
See application file for complete search history.

(56) References Cited

U.S. PATENT DOCUMENTS

| | | | |
|---|---|---|---|
| 6,355,045 B1 | 3/2002 | Gundlapalli | |
| 6,676,662 B1 * | 1/2004 | Bagga .................. | A61F 2/4644 |
| | | | 606/87 |
| 7,124,762 B2 | 10/2006 | Carter | |
| 7,722,608 B2 * | 5/2010 | Steiner ................. | A61F 2/4644 |
| | | | 606/86 R |
| 7,955,336 B2 * | 6/2011 | Gil ........................ | A61F 2/4644 |
| | | | 606/79 |
| 8,795,284 B2 | 8/2014 | Ribeiro | |
| 8,840,619 B2 | 9/2014 | Zajac | |
| 8,852,197 B2 | 10/2014 | Waite | |
| 9,339,294 B2 | 5/2016 | Mandeen | |

(Continued)

FOREIGN PATENT DOCUMENTS

| | | |
|---|---|---|
| WO | 2015164342 A1 | 10/2015 |
| WO | 2017151335 A1 | 9/2017 |
| WO | 2021046235 A1 | 3/2021 |

*Primary Examiner* — Matthew J Lawson
(74) *Attorney, Agent, or Firm* — McDonnell Boehnen Hulbert & Berghoff LLP

(57) ABSTRACT

The present disclosure provides a meniscal allograft transplantation system and methods of use.

20 Claims, 8 Drawing Sheets

(56)     References Cited

U.S. PATENT DOCUMENTS

| | | | | |
|---|---|---|---|---|
| 9,522,022 | B2 | 12/2016 | Cheney | |
| 9,795,397 | B2 | 10/2017 | Collazo | |
| 9,801,726 | B2 | 10/2017 | Karnes | |
| 9,918,769 | B2 * | 3/2018 | Provencher | A61F 2/4644 |
| 10,390,965 | B2 | 8/2019 | Tsukayama | |
| 10,743,892 | B2 | 8/2020 | Krause | |
| 11,213,406 | B2 * | 1/2022 | Rodriguez | A61F 2/4644 |
| 11,452,622 | B2 | 9/2022 | Bosworth | |
| 11,529,147 | B2 | 12/2022 | Frey | |
| 11,534,186 | B2 | 12/2022 | Stemniski | |
| 2002/0082604 | A1 * | 6/2002 | Abdelgany | A61F 2/4644 |
| | | | | 623/16.11 |
| 2008/0255623 | A1 * | 10/2008 | Steiner | B25B 3/00 |
| | | | | 606/86 R |
| 2009/0312801 | A1 | 12/2009 | Lemoine | |
| 2013/0096680 | A1 * | 4/2013 | Ribeiro | A61F 2/4644 |
| | | | | 606/88 |
| 2015/0297361 | A1 * | 10/2015 | Kehres | B25B 5/102 |
| | | | | 83/13 |
| 2016/0270933 | A1 * | 9/2016 | Bosworth | A61F 2/28 |
| 2020/0129241 | A1 | 4/2020 | Forstein | |
| 2020/0360008 | A1 | 11/2020 | Breslich | |
| 2020/0375613 | A1 | 12/2020 | Frey | |
| 2020/0390452 | A1 | 12/2020 | Bojarski | |
| 2021/0007863 | A1 | 1/2021 | Rodriguez | |
| 2021/0113222 | A1 | 4/2021 | Khatibi | |
| 2022/0000564 | A1 | 1/2022 | Mccabe | |
| 2023/0372123 | A1 * | 11/2023 | Jamali | A61F 2/4644 |
| 2024/0197498 | A1 * | 6/2024 | Graul | A61F 2/30942 |
| 2025/0065527 | A1 * | 2/2025 | Cannon | B26D 7/0006 |

* cited by examiner

MENISCAL ALLOGRAFT TRANSPLANTATION SYSTEM AND METHODS FOR USE

CROSS-REFERENCE TO RELATED APPLICATIONS

This application claims priority to U.S. Provisional Application No. 63/511,254 entitled "Meniscal Allograft Transplantation System and Methods for Use," filed on Jun. 30, 2023, the contents of which are hereby incorporated by reference in its entirety

BACKGROUND

Meniscal allograft transplantation is a common technique for total replacement of a torn lateral or medial meniscus. One type of meniscal allograft transplantation utilizes a trapezoidal bone block commonly known as a dovetail meniscal allograft. Such an allograft must be cut to a precise shape. The range in allograft sizes in addition to the geometry of the bone makes cutting of the dovetail meniscal allograft difficult to do by hand. As such, an improved system that cuts the dovetail shape with greater precision to create an allograft that will better fit into the recipient site, effectively decreasing implant failure and improving patient results, is desirable.

In addition, meniscal allograft transplantation requires reaming one or more areas of the tibial bone of the patient to make room for the allograft using a meniscal guide system. Detecting the depth a reamer has penetrated through the tibial bone can be difficult. In particular, existing meniscal guide systems may lack features to prevent surgeons from drilling beyond the tibial bone into a sensitive region of nerves and/or arteries. Accordingly, an improved system incorporating one or more hard stops that prevent the surgeon from drilling past the tibial bone and effectively prevents damage to the nerves and/or arteries of the patient may be desirable.

SUMMARY

The disclosure herein includes a meniscal allograft transplantation system and methods of use.

In particular, in one aspect, the present disclosure provides a device for use in a meniscal allograft transplantation procedure. The device includes a first sidewall and a second sidewall spaced away from the first sidewall at a fixed distance. The device also includes a moveable wall positioned between the first sidewall and the second sidewall. The device also includes an adjustment member coupled to the moveable wall. The adjustment member is configured to alter a distance between the moveable wall and the first sidewall. The device also includes a fixed cutting guide including a first slot. The fixed cutting guide is fixed with respect to the first sidewall. The device also includes a first removable cutting guide including a second slot and a third slot. The first removable cutting guide is configured to be removably coupled to the first sidewall and/or the second sidewall. The device also includes a second removable cutting guide including a fourth slot. The second removable cutting guide is configured to be removably coupled to the first sidewall and/or the second sidewall.

In another aspect, the present disclosure provides a system for use in a meniscal allograft transplantation procedure. The system can include a first guide block including a first through hole, a second through hole, a third through hole, and a fourth through hole. The system can also include a first guidewire configured to be positioned through the first through hole. The system can also include a second guidewire configured to be positioned through the second through hole. The system can also include a third guidewire configured to be positioned through the third through hole. The third guidewire includes a first portion having a first diameter and a second portion having a second diameter that is less than the first diameter. The system can also include a fourth guidewire configured to be positioned through the fourth through hole. The fourth guidewire includes a first portion having a first diameter and a second portion having a second diameter that is less than the first diameter. The system can also include a first hard stop feature configured to be positioned over the third guidewire. The first hard stop feature has an inner diameter greater than the second diameter of the third guidewire but less than the first diameter of the third guidewire. The system can also include a second hard stop feature configured to be positioned over the fourth guidewire. The second hard stop feature has an inner diameter greater than the second diameter of the fourth guidewire but less than the first diameter of the fourth guidewire. The system can also include a second guide block including at least one through hole configured to receive a guidewire. Such a guide block can include at least two, three, four, or five through holes configured to receive a guidewire. The system can also include a second guide block including a first through hole configured to receive the first guidewire, a second through hole configured to receive the second guidewire, a third through hole configured to receive the third guidewire, and a fourth through hole configured to receive the fourth guidewire. The second guide block is configured to contact the first hard stop feature and the second hard stop feature. The system also includes a first reamer configured to be positioned over the first guidewire and through the first through hole of the second guide block. The first reamer includes a third hard stop feature having a diameter greater than a diameter of the first through hole of the second guide block. The system also includes a second reamer configured to be positioned over the second guidewire and through the second through hole of the second guide block. The second reamer includes a fourth hard stop feature having a diameter greater than a diameter of the second through hole of the second guide block.

In another aspect, the present disclosure provides a system for use in a meniscal allograft transplantation procedure. The system includes a handle, a guide base coupled to the handle, and a guidewire hole guide removably coupled to the guide base. The system also includes a first guidewire having a first end and a second end opposite the first end. The first end of the first guidewire is configured to be positioned through a first through hole in the guidewire hole guide. The first guidewire includes a first hard stop feature positioned between the first end and the second end of the first guidewire. The first hard stop feature has a diameter greater than a diameter of the first through hole. The first guidewire includes a reduced diameter portion between the first hard stop feature and the first end of the first guidewire. The system also includes a second guidewire having a first end and a second end opposite the first end. The first end of the second guidewire is configured to be positioned through a second through hole in the guidewire hole guide. The second guidewire includes a second hard stop feature positioned between the first end and the second end of the second guidewire. The second hard stop feature has a diameter greater than a diameter of the second through hole. The second guidewire includes a reduced diameter portion between the second hard stop feature and the second end of the second guidewire. The system also includes a first reamer having a first end and a second end opposite the first end. The first end of the first reamer is configured to be positioned over the first guidewire and through the first through hole of the guidewire hole guide. The first reamer includes a third hard stop feature adjacent the second end of the first reamer. The system also includes a second reamer having a first end and a second end opposite the first end. The first end of the second reamer is configured to be positioned over the second guidewire and through the second through hole of the guidewire hole guide. The second reamer includes a fourth hard stop feature adjacent the second end of the second reamer.

These as well as other aspects, advantages, and alternatives, will become apparent to those of ordinary skill in the art by reading the following detailed description, with reference where appropriate to the accompanying drawings.

DETAILED DESCRIPTION

Figure 1:
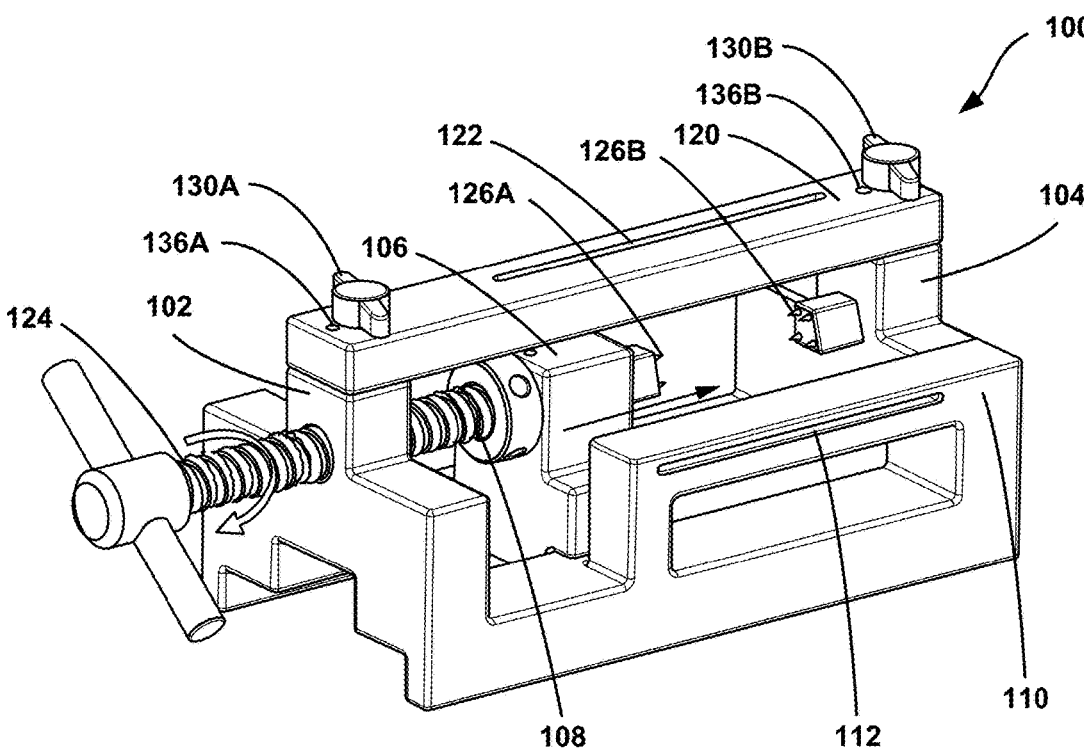
FIG. 1 is a perspective view of an example device for use in a meniscal allograft transplantation procedure.
Figure 2:
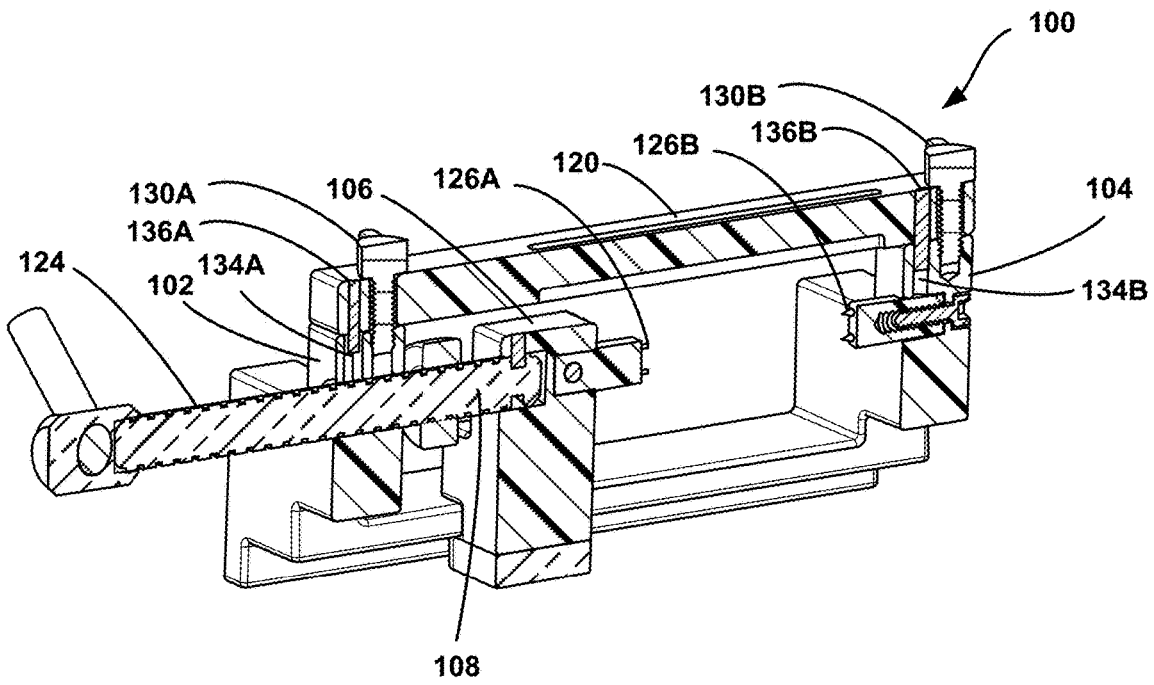
FIG. 2 is a perspective cross-sectional view of the example device of FIG. 1.
Figures 3, 4, 5:
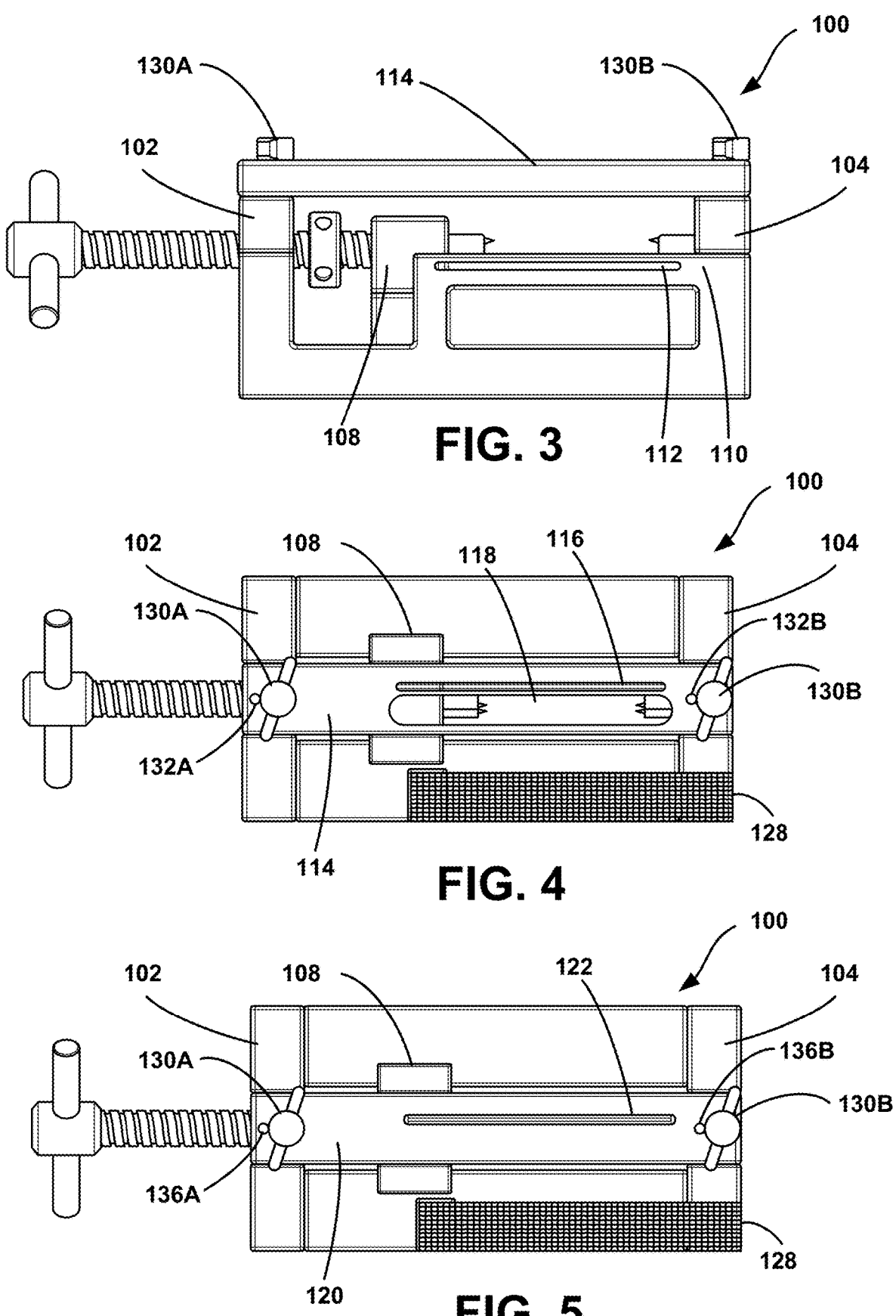
FIG. 3 is side view of the example device of FIG. 1.
FIG. 4 is a top view of the example device of FIG. 1 with a first removable cutting guide positioned thereon.
FIG. 5 is a top view of the example device of FIG. 1 with a second removable cutting guide positioned thereon.
Figure 6:
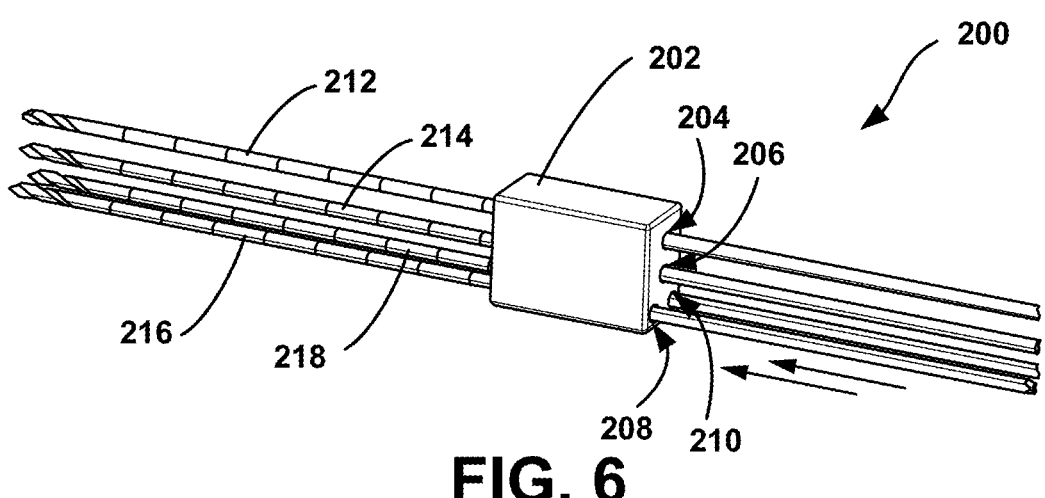
FIG. 6 illustrates a guide block with four guidewires positioned therethrough.
Figure 7:
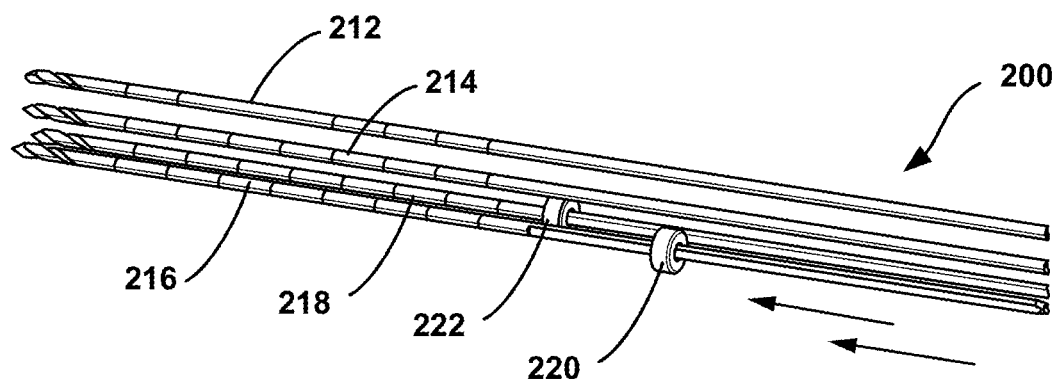
FIG. 7 illustrates a pair of hard stop nuts positioned on a pair of slotted guidewires.
Figure 8:
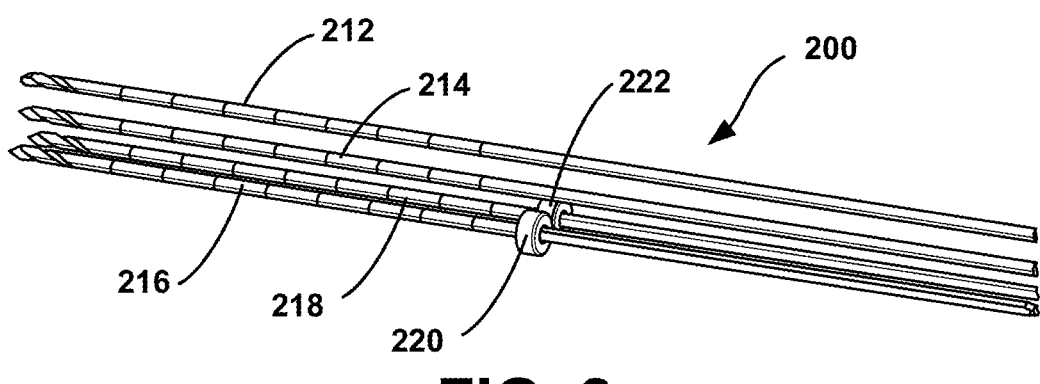
FIG. 8 illustrates a pair of hard stop nuts positioned on a pair of slotted guidewires.

With reference to the Figures, FIGS. 1-5 illustrate a device 100 for use in a meniscal allograft transplantation procedure. As shown in FIGS. 1-5, the device 100 includes a first sidewall 102 and a second sidewall 104 spaced away from the first sidewall 102 at a fixed distance. The device 100 also includes a moveable wall 106 positioned between the first sidewall 102 and the second sidewall 104. The device 100 also includes an adjustment member 108 coupled to the moveable wall 106. The adjustment member 108 is configured to alter a distance between the moveable wall 106 and the first sidewall 102. The device 100 also includes a fixed cutting guide 110 including a first slot 112. The fixed cutting guide 110 is fixed with respect to the first sidewall 102. The device 100 also includes a first removable cutting guide 114 including a second slot 116 and a third slot 118. The first removable cutting guide 114 is configured to be removably coupled to the first sidewall 102 and/or the second sidewall 104. The device 100 also includes a second removable cutting guide 120 including a fourth slot 122. The second removable cutting guide 120 is configured to be removably coupled to the first sidewall 102 and/or the second sidewall 104.

In one example, the adjustment member 108 comprises a threaded rod 124. In such an example, a rotation of the threaded rod 124 in a first direction moves the moveable wall 106 closer to the first sidewall 102, and a rotation of the threaded rod 124 in a second direction moves the moveable wall 106 further from the first sidewall 102.

In one example, the device 100 further includes a first set of teeth 126A coupled to the first sidewall 102, and a second set of teeth 126B coupled to the moveable wall 106. In one example, the first set of teeth 126A are removably coupled to the first sidewall 102, and the second set of teeth 126B are removably coupled to the moveable wall 106. In one example, the first set of teeth 126A and the second set of teeth 126B attach to the first sidewall 102 and the moveable wall 106 with a bolt or other similar coupling mechanism that can be unscrewed to release the first set of teeth 126A and the second set of teeth 126B. This permits easy replacement of the first set of teeth 126A and the second set of teeth 126B as they are worn down, creating a more economical design that only requires two small components to be replaced rather than the entire device.

In one example, the device 100 further includes a rasp surface 128 positioned on a top surface of the fixed cutting guide 110. The rasp surface 128 may be used to file down rough edges of the meniscal allograft left by the sawblade, as discussed in additional detail below. The length of the rasp surface 128 spans the largest allografts needed, allowing the user to file down an edge on a perfectly flat plane and remove material uniformly. This helps maintain the evenness of the surfaces as well as the geometry of the allograft.

In one example, the first removable cutting guide 114 and the second removable cutting guide 120 are removably coupled to the first sidewall 102 and the second sidewall 104 via a first threaded connector 130A and a second threaded connector 130B. In one example, the first removable cutting guide 114 includes a first pin 132A configured to be positioned in a first hole 134A in the first sidewall 102, and the first removable cutting guide 114 includes a second pin 132B configured to be positioned in a second hole 134B in the second sidewall 104. Similarly, in one example, the second removable cutting guide 120 includes a first pin 136A configured to be positioned in the first hole 134A in the first sidewall 102, and the second removable cutting guide 120 includes a second pin 136B configured to be positioned in the second hole 134B in the second sidewall 104. The first pins 132A, 136A and the second pins 132B, 136B in each of the first removable cutting guide 114 and the second removable cutting guide 120 may help align the first removable cutting guide 114 and the second removable cutting guide 120 prior to removably coupling those features to the first sidewall 102 and the second sidewall 104 via the threaded connectors.

In one example, the first slot 112 is positioned substantially perpendicular to the second slot 116, and the fourth slot 122 is positioned at a non-zero angle with respect to the second slot 116 such that the second slot 116 and the fourth slot 122 are not perpendicular.

In use, a meniscal allograft is positioned between the first set of teeth 126A and the second set of teeth 126B, and the adjustment member 108 is used to move the moveable wall 106 closer to the first sidewall 102 to thereby secure the meniscal allograft in place. Once in place, the surgeon makes a first cut with a saw through the first slot 112 to create a bottom cut on the allograft. This allows the creation of a flat surface for the bottom feature of the trapezoidal shape of a dovetail allograft. Next, the surgeon positions the first removable cutting guide 114 onto the device 100. The larger third slot 118 is used to hold the meniscus out of the way of the cut. The surgeon the makes a second cut with a saw through the second slot 116 that is a vertical cut substantially perpendicular to the first cut. Next, the surgeon removes the first removable cutting guide 114 and positions the second removable cutting guide 120 onto the device 100. The surgeon the makes a third cut with a saw through the fourth slot 122 that is angled with respect to the second cut to finish creating the trapezoidal shape of the allograft.

FIGS. 6-14 illustrate a system 200 for use in a meniscal allograft transplantation procedure. As shown in FIGS. 6-14, the system 200 includes a first guide block 202 including a first through hole 204, a second through hole 206, a third through hole 208, and a fourth through hole 210. The system 200 also includes a first guidewire 212 configured to be positioned through the first through hole 204. The system also includes a second guidewire 214 configured to be positioned through the second through hole 206. The system 200 also includes a third guidewire 216 configured to be positioned through the third through hole 208. The third guidewire 216 includes a first portion having a first diameter and a second portion having a second diameter that is less than the first diameter. The system 200 also includes a fourth guidewire 218 configured to be positioned through the fourth through hole 210. The fourth guidewire 218 includes a first portion having a first diameter and a second portion having a second diameter that is less than the first diameter.

The system 200 also includes a first hard stop feature 220 configured to be positioned over the third guidewire 216. The first hard stop feature 220 has an inner diameter greater than the second diameter of the third guidewire 216 but less than the first diameter of the third guidewire 216. The system 200 also includes a second hard stop feature 222 configured to be positioned over the fourth guidewire 218. The second hard stop feature 222 has an inner diameter greater than the second diameter of the fourth guidewire 218 but less than the first diameter of the fourth guidewire 218. In one example, the first hard stop feature 220 and the second hard stop feature 222 each include a ring or a nut.

The system 200 also includes a second guide block 224 including a first through hole 226 configured to receive the first guidewire 212, a second through hole 228 configured to receive the second guidewire 214, a third through hole 230 configured to receive the third guidewire 216, and a fourth through hole 232 configured to receive the fourth guidewire 218. The second guide block 224 is configured to contact the first hard stop feature 220 and the second hard stop feature 222.

The system 200 also includes a first reamer 234 configured to be positioned over the first guidewire 212 and through the first through hole 226 of the second guide block 224. The first reamer 234 includes a third hard stop feature 236 having a diameter greater than a diameter of the first through hole 226 of the second guide block 224. The system 200 also includes a second reamer 238 configured to be positioned over the second guidewire 214 and through the second through hole 228 of the second guide block 224. The second reamer 238 includes a fourth hard stop feature 240 having a diameter greater than a diameter of the second through hole 228 of the second guide block 224.

In one example, the third guidewire 216 comprises a slotted guidewire such that the second portion of the third guidewire 216 includes a first flat portion and a second flat portion opposite the first flat portion. In one example, the fourth guidewire 218 comprises a slotted guidewire such that the second portion of the fourth guidewire 218 includes a first flat portion and a second flat portion opposite the first flat portion.

In one example, the first through hole 204 of the first guide block 202, the second through hole 206 of the first guide block 202, the third through hole 208 of the first guide block 202, and the fourth through hole 210 of the first guide block 202 are equal.

In one example, a diameter of the first reamer 234 is less than a diameter of the second reamer 238. In one particular example, the diameter of the first reamer 234 is about 6 mm, and the diameter of the second reamer 238 is about 7 mm.

In use, the first guidewire 212 and the second guidewire 214 are positioned through the first through hole 204 and the second through hole 206 of the first guide block 202, respectively, and into the tibial bone of the patient to a desired depth. Next, the third guidewire 216 and the fourth guidewire 218 are positioned through the third through hole 208 and the fourth through hole 210 of the first guide block 202, respectively, and into the tibial bone of the patient to the desired depth so that they align with the desired depth of the first guidewire 212 and the second guidewire 214. Next, the first hard stop feature 220 is positioned over the second portion of the third guidewire 216 and moved along the third guidewire 216 until the first hard stop feature 220 meets the first portion of the third guidewire 216. Since the diameter of the first portion of the third guidewire 216 is greater than an inner diameter of the first hard stop feature 220, the first hard stop feature 220 cannot be pushed any further along the third guidewire 216. Similarly, the second hard stop feature 222 is positioned over the second portion of the fourth guidewire 218 and moved along the fourth guidewire 218 until the second hard stop feature 222 meets the first portion of the fourth guidewire 218. Since the diameter of the first portion of the fourth guidewire 218 is greater than an inner diameter of the second hard stop feature 222, the second hard stop feature 222 cannot be pushed any further along the fourth guidewire 218.

Figure 9:
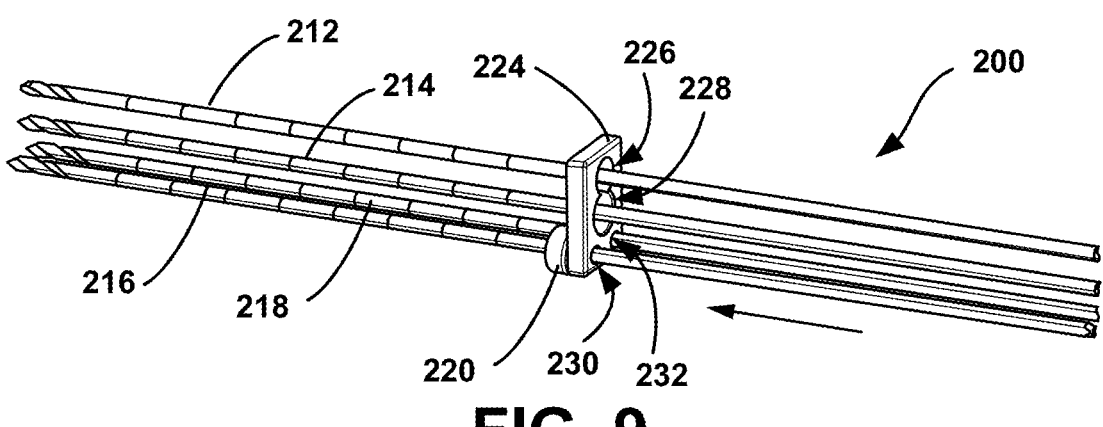
FIG. 9 illustrates a reamer guide block positioned over the four guidewires.
Figure 10:
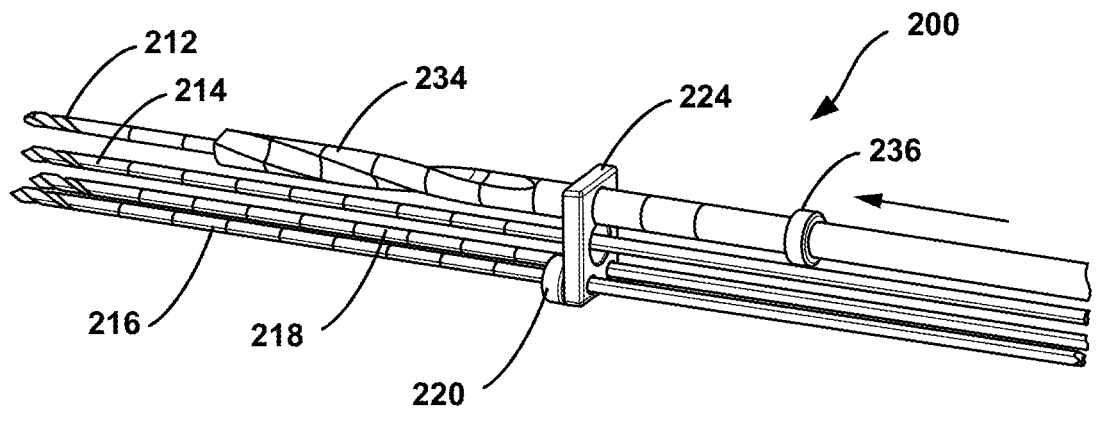
FIG. 10 illustrates a first reamer positioned over one of the guidewires.
Figure 11:
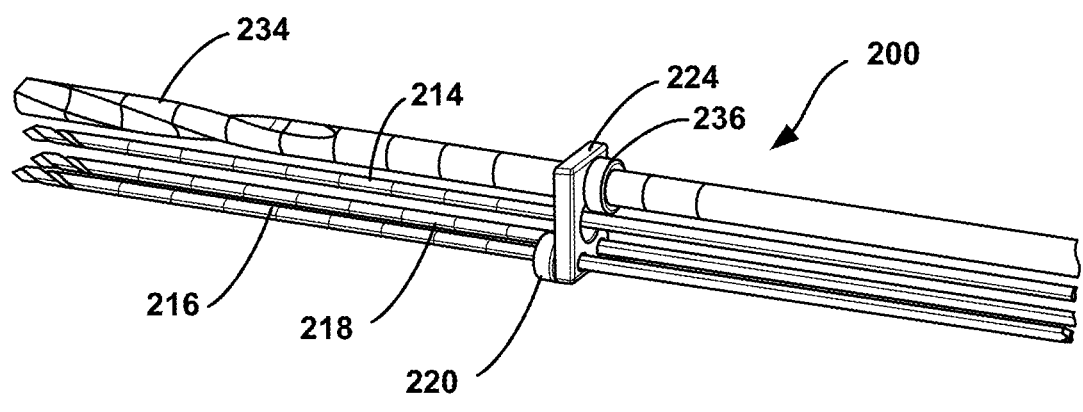
FIG. 11 illustrates the first reamer positioned over one of the guidewires.
Figure 12:
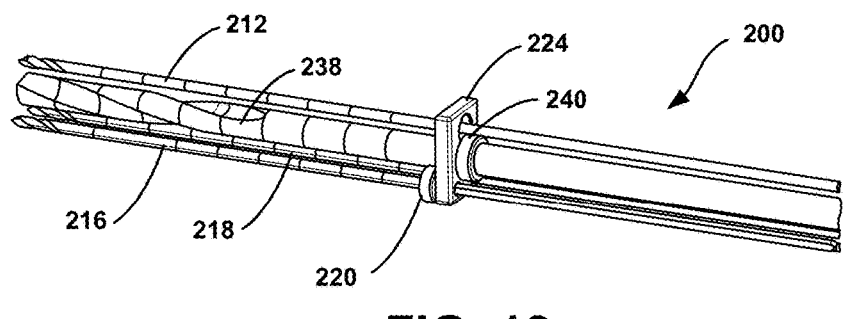
FIG. 12 illustrates a second reamer positioned over another one of the guidewires.
Figure 13:
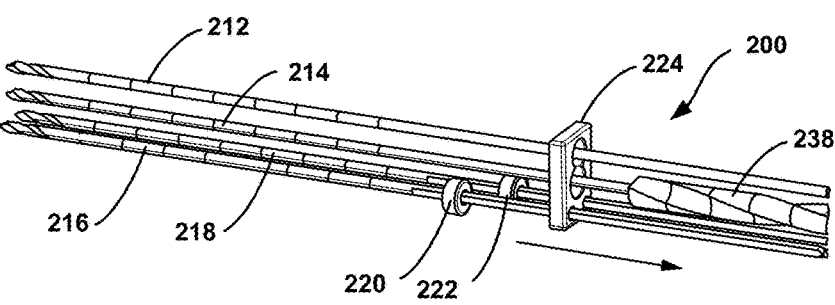
FIG. 13 illustrates the second reamer being removed from the guidewire.
Figure 14:
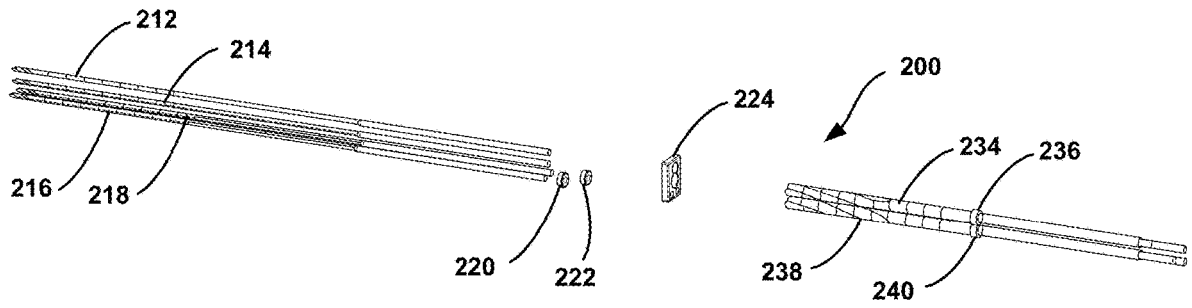
FIG. 14 illustrates the components of the system being disassembled.
Figure 15:
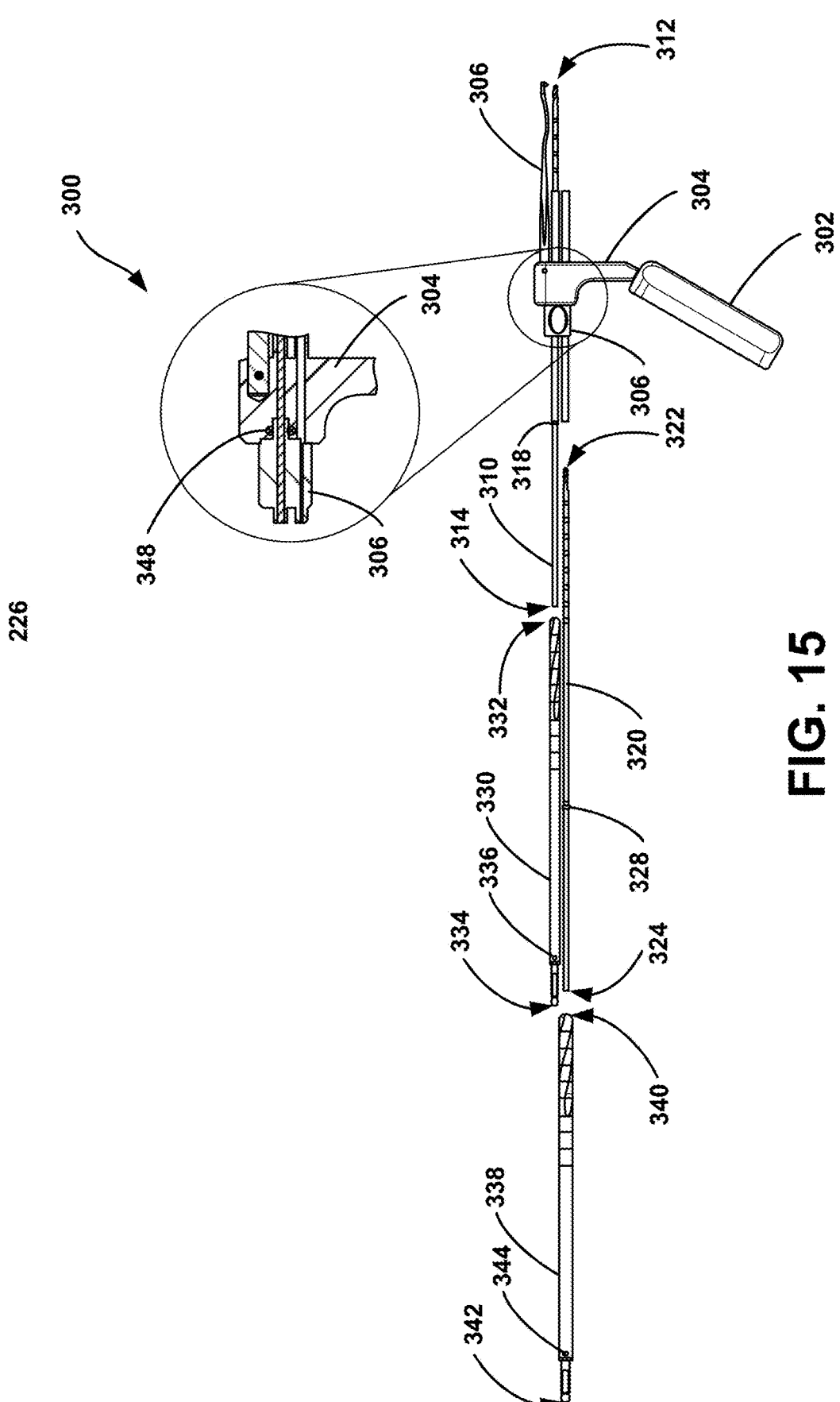
FIG. 15 illustrates a side view of an example system for use in a meniscal allograft transplantation procedure.

Next, the second guide block 224 is positioned over each of the first guidewire 212, the second guidewire 214, the third guidewire 216, and the fourth guidewire 218 as shown in FIG. 9 until the second guide block 224 reaches the first hard stop feature 220 and the second hard stop feature 222 and cannot be pushed any further. The first reamer 234 is then positioned over the first guidewire 212 and drilled until the third hard stop feature 236 of the first reamer 234 contacts the second guide block 224. As shown in FIG. 11, the third hard stop feature 236 has a diameter greater than a diameter of the first through hole 226 of the second guide block 224. Next, the second reamer 238 is then positioned over the second guidewire 214 and drilled until the fourth hard stop feature 240 of the second reamer 238 contacts the second guide block 224. As shown in FIG. 12, the fourth hard stop feature 240 has a diameter greater than a diameter of the second through hole 228 of the second guide block 224. All parts of the system 200 may then be removed from the patient.

FIGS. 15-18 illustrate another system 300 for use in a meniscal allograft transplantation procedure. As shown in FIGS. 15-18, the system 300 includes a handle 302, a guide base 304 coupled to the handle 302, and a guidewire hole guide 306 removably coupled to the guide base 304. In one example, the system 300 also includes a marking hook shaft 308 coupled to the guide base 304. The system 300 also includes a first guidewire 310 having a first end 312 and a second end 314 opposite the first end 312. The first end 312 of the first guidewire 310 is configured to be positioned through a first through hole 316 in the guidewire hole guide 306. The first guidewire 310 includes a first hard stop feature 318 positioned between the first end 312 and the second end 314 of the first guidewire 310. The first hard stop feature 318 has a diameter greater than a diameter of the first through hole 316. The first guidewire 310 includes a reduced diameter portion between the first hard stop feature 318 and the first end 312 of the first guidewire 310. The system 300 also includes a second guidewire 320 having a first end 322 and a second end 324 opposite the first end 322. The first end 322 of the second guidewire 320 is configured to be positioned through a second through hole 326 in the guidewire hole guide 306. The second guidewire 320 includes a second hard stop feature 328 positioned between the first end 322 and the second end 324 of the second guidewire 320. The second hard stop feature 328 has a diameter greater than a diameter of the second through hole 326. The second guidewire 320 includes a reduced diameter portion between the second hard stop feature 328 and the second end 324 of the second guidewire 320.

The system 300 also includes a first reamer 330 having a first end 332 and a second end 334 opposite the first end 332. The first end 332 of the first reamer 330 is configured to be positioned over the first guidewire 310 and through the first through hole 316 of the guidewire hole guide 306. The first reamer 330 includes a third hard stop feature 336 adjacent the second end 334 of the first reamer 330. The system 300 also includes a second reamer 338 having a first end 340 and a second end 342 opposite the first end 340. The first end 340 of the second reamer 338 is configured to be positioned over the second guidewire 320 and through the second through hole 326 of the guidewire hole guide 306. The second reamer 338 includes a fourth hard stop feature 344 adjacent the second end 342 of the second reamer 338.

In one example, a diameter of the first reamer 330 is less than a diameter of the second reamer 338. In one such example, the diameter of the first reamer 330 is about 6 mm, and wherein the diameter of the second reamer 338 is about 7 mm.

Figure 16:
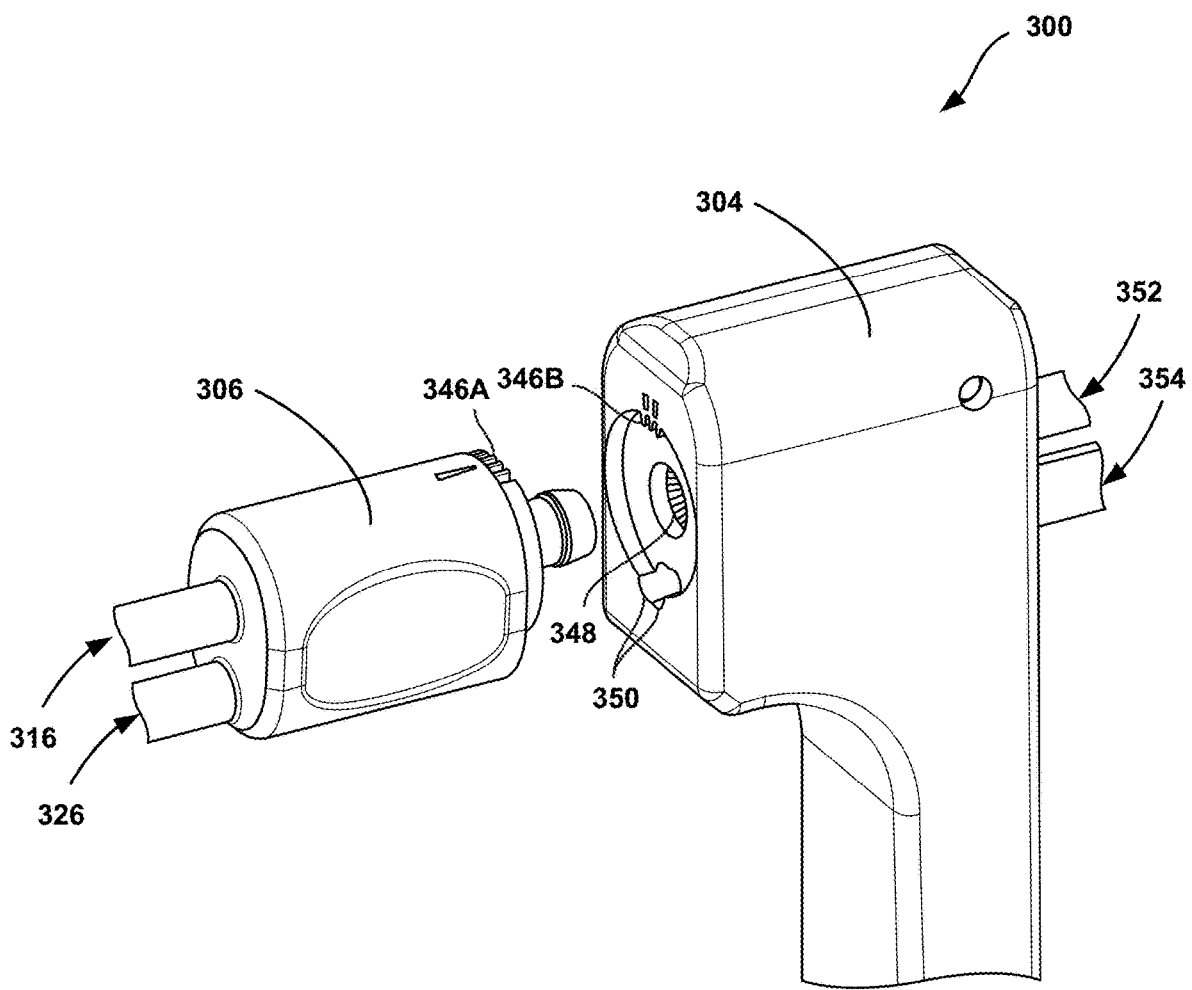
FIG. 16 illustrates a guide base of the system of FIG. 15.

As shown in FIG. 16, in one example, the guidewire hole guide 306 includes a first plurality of teeth 346A configured to interact with a second plurality of teeth 346B on the guide base 304 to provide a variety of rotational arrangements between the guidewire hole guide 306 and the guide base 304 and further to prevent rotation of the guidewire hole guide 306 with respect to the guide base 304. Such an arrangement permits the formation of a left- and right-winged dovetail. The guidewire hole guide 306 can be inserted into the guide base 304 in two positions by rotating about its center axis and aligning the arrow on the guide base 304 with the position marks. The first plurality of teeth 346A and the second plurality of teeth 346B ensure the guidewire hole guide 306 and the guide base 304 are locked at the desired angle and unable to rotate freely. In one example, the guide base 304 includes a canted coil spring 348 to removably couple the guidewire hole guide 306 to the guide base 304. The canted coil spring 348 creates a snap-lock mechanism that secures the guidewire hole guide 306 in place. This prevents the guidewire hole guide 306 and the guide base 304 from separating while still permitting the user to disassemble it later for bidirectional use. When the parts are assembled, the system 300 is locked in place, and the first through hole 316 of the guidewire hole guide 306 is aligned with a single channel 350 on the guide base 304.

In one example, the reduced diameter portion of the first guidewire 310 is positioned adjacent the first hard stop feature 318, and the reduced diameter portion of the second guidewire 320 is positioned adjacent the second hard stop feature 328.

In one example, the guide base 304 includes a first through hole 352 aligned with the first through hole 316 of the guidewire hole guide 306 when the guidewire hole guide 306 is removably coupled to the guide base 304, and the guide base 304 includes a second through hole 354 aligned with the second through hole 326 of the guidewire hole guide 306 when the guidewire hole guide 306 is removably coupled to the guide base 304.

Figure 17:
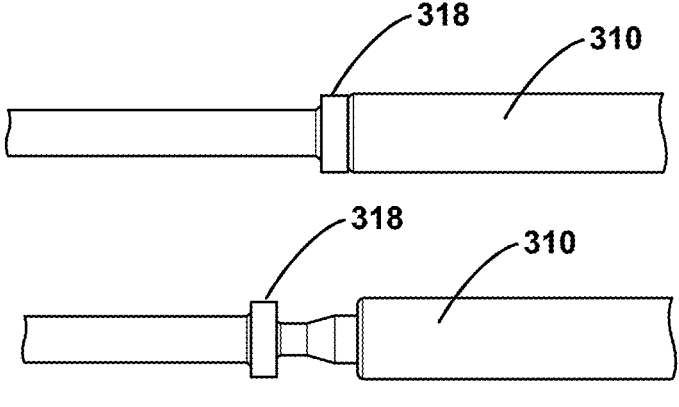
FIG. 17 illustrates a guidewire of the system of FIG. 15.

In use, a surgeon uses a point on the marking hook shaft 308 of the system 300 to locate the edge of the tibia—the furthest point that will be drilled. The guidewire hole guide 306 is connected to the guide base 304 at the desired position (as discussed above in relation to FIG. 16). The surgeon can then drill the first guidewire 310 through the first through hole 316 in the guidewire hole guide 306 and drill the second guidewire 320 through the second through hole 326 in the guidewire hole guide 306. The hard stop features on the drill guide prevents overdrilling past the tibia. As shown in FIG. 17, the first hard stop feature 318 may comprise a ring feature that is wider than the diameter of the first through hole 316 in the guidewire hole guide 306. Similarly, the first hard stop feature 328 may comprise a ring feature that is wider than the diameter of the second through hole 326 in the guidewire hole guide 306. As such, the first hard stop feature 318 and the second hard stop feature 328 create a precise point at which the surgeon cannot drill past. The the first hard stop feature 318 and the second hard stop feature 328 perfectly align the tip of the first guidewire 310 and the second guidewire 320, respecitvely, with the point of the marking hook shaft 308. The first guidewire 310 and the second guidewire 320 may each include a thinned diameter located before the first hard stop feature 318 and the second hard stop feature 328, respectively. This creates a breakaway point that the surgeon can snap off the back end of the first guidewire 310 and the second guidewire 320 after placement in the tibial bone. The entire guide system (excluding the first guidewire 310 and the second guidewire 320) can then be removed from the patient.

Figure 18:
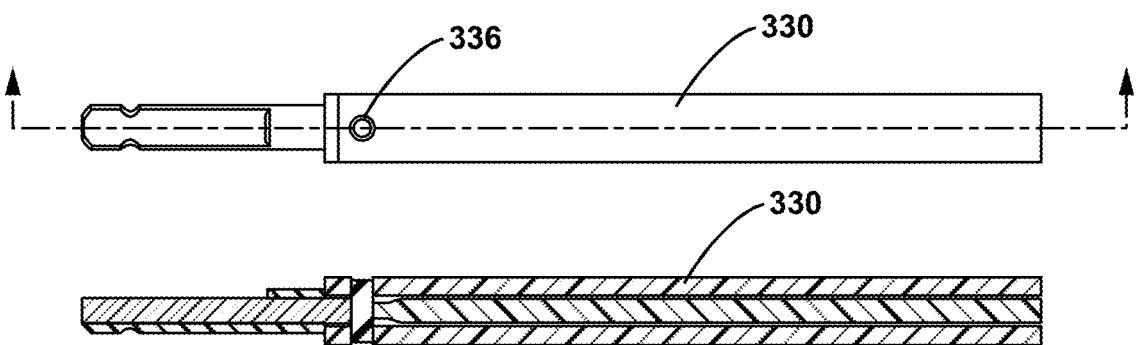
FIG. 18 illustrates a reamer of the system of FIG. 15.

Next, the surgeon can then ream over the first guidewire 310 and the second guidewire 320 with the respective cannulated reamers to create the dovetail-shaped slot in the tibia. In particular, the surgeon reams over the first guidewire 310 with the smaller diameter first reamer 330 and over the second guidewire 320 with the larger diameter second reamer 338. The first reamer 330 has a third hard stop feature 336 and the fourth reamer 338 has fourth hard stop feature 344. In one example, as shown in FIG. 18, the third hard stop feature 336 and the fourth hard stop feature 344 each comprise a pin inserted at the end of the first reamer 330 and second reamer 338, respectively. The third hard stop feature 336 stops the surgeon from drilling beyond the end of the snapped first guidewire 310 since the third hard stop feature 336 contacts the end of the snapped first guidewire 310 when the first reamer 330 reaches the desired depth. Similarly, the fourth hard stop feature 344 stops the surgeon from drilling beyond the end of the snapped second guidewire 320 since the fourth hard stop feature 344 contacts the end of the snapped second guidewire 320 when the second reamer 338 reaches the desired depth. The third hard stop feature 336 and the fourth hard stop feature 344 perfectly aligns the end of the first reamer 330 and the second reamer 338, respectively, with the point of the marking hook shaft 308, preventing overdrilling into the neurons behind the tibia.

It should be understood that arrangements described herein are for purposes of example only. As such, those skilled in the art will appreciate that other arrangements and other elements (e.g. machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location, or other structural elements described as independent structures may be combined.

While various aspects and examples have been disclosed herein, other aspects and examples will be apparent to those skilled in the art. The various aspects and examples disclosed herein are for purposes of illustration and are not intended to be limiting, with the true scope being indicated by the following claims, along with the full scope of equivalents to which such claims are entitled. It is also to be understood that the terminology used herein is for the purpose of describing particular examples only, and is not intended to be limiting.

Example methods and systems are described herein. It should be understood that the words "example," "exemplary," and "illustrative" are used herein to mean "serving as an example, instance, or illustration." Any example or feature described herein as being an "example," being "exemplary," or being "illustrative" is not necessarily to be construed as preferred or advantageous over other examples or features. The examples described herein are not meant to be limiting. It will be readily understood that the aspects of the present disclosure, as generally described herein, and illustrated in the figures, can be arranged, substituted, combined, separated, and designed in a wide variety of different configurations, all of which are explicitly contemplated herein.

Furthermore, the particular arrangements shown in the Figures should not be viewed as limiting. It should be understood that other examples may include more or less of each element shown in a given Figure. Further, some of the illustrated elements may be combined or omitted. Yet further, an example may include elements that are not illustrated in the Figures.

In the following description, numerous specific details are set forth to provide a thorough understanding of the disclosed concepts, which may be practiced without some or all of these particulars. In other instances, details of known devices and/or processes have been omitted to avoid unnecessarily obscuring the disclosure. While some concepts will be described in conjunction with specific examples, it will be understood that these examples are not intended to be limiting.

As used herein, "coupled" means associated directly as well as indirectly. For example, a member A may be directly associated with a member B, or may be indirectly associated therewith, e.g., via another member C. It will be understood that not all relationships among the various disclosed elements are necessarily represented.

Unless otherwise indicated, the terms "first," "second," etc. are used herein merely as labels, and are not intended to impose ordinal, positional, or hierarchical requirements on the items to which these terms refer. Moreover, reference to, e.g., a "second" item does not require or preclude the existence of, e.g., a "first" or lower-numbered item, and/or, e.g., a "third" or higher-numbered item.

Reference herein to "one embodiment" or "one example" or "an example" means that one or more feature, structure, or characteristic described in connection with the example is included in at least one implementation. The phrases "one embodiment" or "one example" or "an example" in various places in the specification may or may not be referring to the same example.

As used herein, a system, apparatus, structure, article, element, component, or hardware "configured to" perform a specified function is indeed capable of performing the specified function without any alteration, rather than merely having potential to perform the specified function after further modification. In other words, the system, apparatus, structure, article, element, component, or hardware "configured to" perform a specified function is specifically selected, created, implemented, utilized, programmed, and/or designed for the purpose of performing the specified function. As used herein, "configured to" denotes existing characteristics of a system, apparatus, structure, article, element, component, or hardware which enable the system, apparatus, structure, article, element, component, or hardware to perform the specified function without further modification. For purposes of this disclosure, a system, apparatus, structure, article, element, component, or hardware described as being "configured to" perform a particular function may additionally or alternatively be described as being "adapted to" and/or as being "operative to" perform that function.

The limitations of the following claims are not written in means-plus-function format and are not intended to be interpreted based on 35 U.S.C. § 112 (f), unless and until such claim limitations expressly use the phrase "means for" followed by a statement of function void of further structure.

By the term "about," "approximately," or "substantially" with reference to amounts or measurement values described herein, it is meant that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide. For example, in one embodiment, the term "about" can refer to +5% of a given value.

Illustrative, non-exhaustive examples, which may or may not be claimed, of the subject matter according the present disclosure are provided below.

What is claimed is:

1. A device comprising:
a first sidewall;
a second sidewall spaced away from the first sidewall at a fixed distance;
a moveable wall positioned between the first sidewall and the second sidewall;
an adjustment member coupled to the moveable wall, wherein the adjustment member is configured to alter a distance between the moveable wall and the first sidewall, wherein the adjustment member comprises a threaded rod, and wherein rotation of the threaded rod in a first direction moves the moveable wall closer to the first sidewall, and wherein rotation of the threaded rod in a second direction moves the moveable wall further from the first sidewall;

a fixed cutting guide including a first slot, wherein the fixed cutting guide is fixed with respect to the first sidewall;

a first removable cutting guide including a second slot and a third slot, wherein the first removable cutting guide is configured to be removably coupled to the first sidewall and/or the second sidewall; and a second removable cutting guide including a fourth slot, wherein the second removable cutting guide is configured to be removably coupled to the first sidewall and/or the second sidewall.

2. The device of claim 1, further comprising:

a first set of teeth coupled to the first sidewall; and a second set of teeth coupled to the moveable wall.

3. The device of claim 2, wherein the first set of teeth are removably coupled to the first sidewall, and wherein the second set of teeth are removably coupled to the moveable wall.

4. The device of claim 1, further comprising:

a rasp surface positioned on a top surface of the fixed cutting guide.

5. The device of claim 1, wherein the first removable cutting guide and the second removable cutting guide are removably coupled to the first sidewall and the second sidewall via a first threaded connector and a second threaded connector.

6. The device of claim 1, wherein the first removable cutting guide includes a first pin configured to be positioned in a first hole in the first sidewall, and wherein the first removable cutting guide includes a second pin configured to be positioned in a second hole in the second sidewall.

7. The device of claim 1, wherein the second removable cutting guide includes a first pin configured to be positioned in a first hole in the first sidewall, and wherein the second removable cutting guide includes a second pin configured to be positioned in a second hole in the second sidewall.

8. The device of claim 1, wherein the first slot is positioned substantially perpendicular to the second slot, and wherein the fourth slot is positioned at a non-zero angle with respect to the second slot such that the second slot and the fourth slot are not perpendicular.

9. A device comprising:

a first sidewall;

a second sidewall spaced away from the first sidewall at a fixed distance;

a moveable wall positioned between the first sidewall and the second sidewall;

an adjustment member coupled to the moveable wall, wherein the adjustment member is configured to alter a distance between the moveable wall and the first sidewall;

a fixed cutting guide including a first slot, wherein the fixed cutting guide is fixed with respect to the first sidewall;

a rasp surface positioned on a top surface of the fixed cutting guide;

a first removable cutting guide including a second slot and a third slot, wherein the first removable cutting guide is configured to be removably coupled to the first sidewall and/or the second sidewall; and a second removable cutting guide including a fourth slot, wherein the second removable cutting guide is configured to be removably coupled to the first sidewall and/or the second sidewall.

10. The device of claim 9, further comprising:

a first set of teeth coupled to the first sidewall; and a second set of teeth coupled to the moveable wall, wherein the first set of teeth are removably coupled to the first sidewall, and wherein the second set of teeth are removably coupled to the moveable wall.

11. The device of claim 9, wherein the first removable cutting guide and the second removable cutting guide are removably coupled to the first sidewall and the second sidewall via a first threaded connector and a second threaded connector.

12. The device of claim 9, wherein the first removable cutting guide includes a first pin configured to be positioned in a first hole in the first sidewall, and wherein the first removable cutting guide includes a second pin configured to be positioned in a second hole in the second sidewall.

13. The device of claim 9, wherein the second removable cutting guide includes a first pin configured to be positioned in a first hole in the first sidewall, and wherein the second removable cutting guide includes a second pin configured to be positioned in a second hole in the second sidewall.

14. The device of claim 9, wherein the first slot is positioned substantially perpendicular to the second slot, and wherein the fourth slot is positioned at a non-zero angle with respect to the second slot such that the second slot and the fourth slot are not perpendicular.

15. A device comprising:

a first sidewall;

a second sidewall spaced away from the first sidewall at a fixed distance;

a moveable wall positioned between the first sidewall and the second sidewall;

an adjustment member coupled to the moveable wall, wherein the adjustment member is configured to alter a distance between the moveable wall and the first sidewall;

a fixed cutting guide including a first slot, wherein the fixed cutting guide is fixed with respect to the first sidewall;

a first removable cutting guide including a second slot and a third slot, wherein the first removable cutting guide is configured to be removably coupled to the first sidewall and/or the second sidewall; and a second removable cutting guide including a fourth slot, wherein the second removable cutting guide is configured to be removably coupled to the first sidewall and/or the second sidewall, wherein the first slot is positioned substantially perpendicular to the second slot, and wherein the fourth slot is positioned at a non-zero angle with respect to the second slot such that the second slot and the fourth slot are not perpendicular.

16. The device of claim 15, further comprising:

a first set of teeth coupled to the first sidewall; and a second set of teeth coupled to the moveable wall.

17. The device of claim 16, wherein the first set of teeth are removably coupled to the first sidewall, and wherein the second set of teeth are removably coupled to the moveable wall.

18. The device of claim 15, wherein the first removable cutting guide and the second removable cutting guide are removably coupled to the first sidewall and the second sidewall via a first threaded connector and a second threaded connector.

19. The device of claim 15, wherein the first removable cutting guide includes a first pin configured to be positioned in a first hole in the first sidewall, and wherein the first removable cutting guide includes a second pin configured to be positioned in a second hole in the second sidewall.

20. The device of claim 15, wherein the second removable cutting guide includes a first pin configured to be positioned in a first hole in the first sidewall, and wherein the second removable cutting guide includes a second pin configured to be positioned in a second hole in the second sidewall.

* * * * *